US009382171B2

(12) United States Patent
Soled et al.

(10) Patent No.: US 9,382,171 B2
(45) Date of Patent: Jul. 5, 2016

(54) IRIDIUM-CONTAINING CATALYSTS, THEIR PRODUCTION AND USE

(71) Applicant: ExxonMobil Chemical Patents Inc., Baytown, TX (US)

(72) Inventors: Stuart L. Soled, Pittstown, NJ (US); Sabato Miseo, Pittstown, NJ (US); Joseph E. Baumgartner, Califon, NJ (US); Christine E. Kliewer, Clinton, NJ (US); Jane C. Cheng, Bridgewater, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/336,312

(22) Filed: Jul. 21, 2014

(65) Prior Publication Data

US 2014/0330058 A1 Nov. 6, 2014

Related U.S. Application Data

(62) Division of application No. 13/512,620, filed as application No. PCT/US2010/061027 on Dec. 17, 2010, now abandoned.

(60) Provisional application No. 61/301,794, filed on Feb. 5, 2010, provisional application No. 61/301,799, filed on Feb. 5, 2010, provisional application No. 61/334,784, filed on May 14, 2010.

(51) Int. Cl.
*C07C 2/74* (2006.01)
*C07C 5/31* (2006.01)
(Continued)

(52) U.S. Cl.
CPC ............... *C07C 2/74* (2013.01); *B01J 23/468* (2013.01); *B01J 37/0203* (2013.01); *B01J 37/08* (2013.01);
(Continued)

(58) Field of Classification Search
CPC .............. C07C 2/54; C07C 2/64; C07C 2/66; C07C 2/74; C07C 5/00; C07C 5/10; C07C 5/11; C07C 15/00; C07C 15/02; C07C 15/04; C07C 13/16; C07C 13/18; C07C 13/19
USPC ......... 585/251, 252, 315, 316–320, 323, 700, 585/940
See application file for complete search history.

(56) References Cited

U.S. PATENT DOCUMENTS 3,194,843 A 7/1965 Silber et al.
3,308,069 A 3/1967 Wadlinger et al.
(Continued)

FOREIGN PATENT DOCUMENTS

EP 0 328 507 8/1989
EP 1 050 339 11/2000
(Continued)

OTHER PUBLICATIONS

Du et al., "*The Chemistry of Selective Ring-Opening Catalysts*", Applied Catalysis A: General, 2005, vol. 294, No. 1, pp. 1-21.
(Continued)

*Primary Examiner* — In Suk Bullock
*Assistant Examiner* — Philip Louie
(74) *Attorney, Agent, or Firm* — Stephen A. Baehl

(57) ABSTRACT

A process is described for producing a catalyst composition comprising an iridium component dispersed on a support. In the process, silica- o group to form an organic iridium complex on the support. The treated support is then heated in an oxidizing atmosphere at a temperature of about 325° C. to about 475° C. to partially decompose the organic metal complex on the support. The treated support is then heated in a reducing atmosphere at a temperature of about 350° C. to about 500° C. to convert the partially decomposed organic iridium complex into the desired iridium component.

6 Claims, 3 Drawing Sheets

(51) Int. Cl.
- *B01J 23/46* (2006.01)
- *B01J 37/02* (2006.01)
- *B01J 37/08* (2006.01)
- *C07C 13/28* (2006.01)
- *C07C 5/00* (2006.01)

(52) U.S. Cl.
CPC ... *C07C 5/00* (2013.01); *C07C 5/31* (2013.01); *C07C 13/28* (2013.01); *C07C 2101/12* (2013.01); *C07C 2521/08* (2013.01); *C07C 2531/08* (2013.01); *Y02P 20/52* (2015.11)

(56) References Cited

U.S. PATENT DOCUMENTS

| | | |
|---|---|---|
| 3,358,044 A | 12/1967 | Russell et al. |
| 3,442,958 A | 5/1969 | Choo |
| 3,514,492 A | 5/1970 | Juguin et al. |
| 3,519,575 A | 7/1970 | Bozik et al. |
| 3,534,110 A | 10/1970 | Juguin et al. |
| 3,534,116 A | 10/1970 | Fuller |
| 3,580,970 A | 5/1971 | Swift |
| 3,691,102 A | 9/1972 | Swift |
| 3,761,428 A | 9/1973 | Sugier et al. |
| 3,843,560 A | 10/1974 | Hayes |
| 3,856,661 A | 12/1974 | Sugier et al. |
| RE28,341 E | 2/1975 | Wadlinger et al. |
| 3,962,362 A | 6/1976 | Suggitt |
| 4,070,413 A | 1/1978 | Imai |
| 4,094,918 A | 6/1978 | Murtha et al. |
| 4,122,125 A | 10/1978 | Murtha et al. |
| 4,147,726 A | 4/1979 | Wu |
| 4,177,165 A | 12/1979 | Murtha et al. |
| 4,206,082 A | 6/1980 | Murtha et al. |
| 4,417,076 A | 11/1983 | Rozovsky et al. |
| 4,418,237 A | 11/1983 | Imai |
| 4,501,926 A | 2/1985 | LaPierre et al. |
| 4,788,371 A | 11/1988 | Imai et al. |
| 4,891,458 A | 1/1990 | Innes et al. |
| 4,929,762 A | 5/1990 | Matsunaga et al. |
| 4,933,507 A | 6/1990 | Inoki et al. |
| 5,053,571 A | 10/1991 | Makkee |
| 5,256,348 A | 10/1993 | Waller |
| 5,811,624 A | 9/1998 | Hantzer et al. |
| 5,906,729 A | 5/1999 | Chou |
| 6,037,513 A | 3/2000 | Chang et al. |
| 6,489,529 B1 | 12/2002 | Cheng et al. |
| 7,285,685 B2 | 10/2007 | Walsdorff et al. |
| 7,538,066 B2 | 5/2009 | Soled et al. |
| 7,563,358 B2 | 7/2009 | Stavens et al. |
| 7,579,511 B1* | 8/2009 | Dakka et al. ............ 585/316 |
| 7,605,107 B2 | 10/2009 | Soled et al. |
| 2002/0038068 A1* | 3/2002 | Baird et al. ............ 585/700 |
| 2006/0166809 A1* | 7/2006 | Malek et al. ............ 502/20 |
| 2007/0032681 A1 | 2/2007 | Walsdorff et al. |
| 2010/0075842 A1 | 3/2010 | Han et al. |

FOREIGN PATENT DOCUMENTS

| | | |
|---|---|---|
| EP | 1 288 188 | 3/2003 |
| GB | 514587 | 11/1939 |
| JP | 58-067636 | 4/1983 |
| JP | 2007/269522 | 10/2007 |
| WO | 91/06616 | 5/1991 |
| WO | 00/67902 | 11/2000 |
| WO | 2009/131769 | 10/2009 |

OTHER PUBLICATIONS

Galperin et al., "*Effect of Support Acid-Basic Properties on Activity and Selectivity of Pt Catalysts in Reaction of Methylcyclopentane Ring Opening*", Applied Catalysis A: General, 2003, vol. 239, No. 1-2, pp. 297-304.

Gault, "*Mechanisma of Skeletal Isomerization of Hydrocarbons on Metals*", Advances in Catalysis, 1981, vol. 30, pp. 1-95.

Gonzales-Cortes et al., "*Tuning the Ring-Opening Reaction of 1,3-dimethylcyclohexane with the Addition of Potassium Over Ir-Containing Catalysts*", Chemical Engineering Journal, 2008, vol. 139, pp. 147-156.

Koshel et al. "A Commercial Synthesis of Phenylcyclohexane ((PHCH)) by the Hydrodimerization of Benzene", Neftekhimiya, 1977, vol. 17, pp. 5705-5709.

Smirniotis et al., "Comparison Between Zeolite β and γ-Al2O3 Supported PT for Reforming Reactions", Journal of Catalysis, 1993, vol. 140, pp. 526-542.

Smirniotis et al., "Increased Aromatization in the Reforming of Mixtures of N-Hexane, Methylcyclopentane and Methylcyclohexane Over Composites of Pt/BaKL Zeolite with Pt/beta or Pt/USY Zeolites", Applied Catalysis A: General, 1995, vol. 123, No. 1, pp. 59-88.

Spieker et al., "*Experimental Investigation and Modeling of Platinum Adsorption onto Ion-modified Silica and Alumina*", Studies in Surface Science and Catalysis, vol. 130, pp. 203-208, 2000.

Soled et al., "Supported Metal Catalysts: Some Interesting New Leads in an Old Field", Scientific Bases for the Preparation of Heterogeneous Catalysts, 2006, vol. 162, pp. 103-110.

Swift, H. et al., "*Metallic Phases and Activites of Nickel-Tin-Silica Catalysts Dehydrogenation of Cyclohexanone, Cyclohexanol, and Cyclohexane*", Journal of Catalysis, 1968, vol. 12, pp. 5-14.

Milczanowski, S., et al., "*Catalytic Dehydrogenation of Cyclohexanone to Phenol*", PrZEMYSL Cheniczny, 1978, vol. 57, No. 3, pp. 129-130—English Abstract Only.

Waligora, B., et al., "*Catalytic Dehydrogenation of Mixture of Cyclohexanol and Cyclohexanon to Phenol*", Prace Chemiczne, 1982, vol. 27, pp. 93-99—English Abstract Only.

* cited by examiner

IRIDIUM-CONTAINING CATALYSTS, THEIR PRODUCTION AND USE

PRIORITY CLAIM

This application is a divisional of and claims priority to U.S. patent application Ser. No. 13/512,620, filed Jul. 12, 2012, which is a National Stage Application of International Application No. PCT/US2010/061027 filed Dec. 17, 2010, which claims priority to U.S. Provisional Application Ser. No. 61/301,794 filed Feb. 5, 2010; U.S. Provisional Application Ser. No. 61/301,799 filed Feb. 5, 2010; and U.S. Provisional Application Ser. No. 61/334,784 filed May 14, 2010, the disclosures of which are fully incorporated herein by their reference.

CROSS REFERENCE TO RELATED APPLICATIONS

This patent application is related to U.S. Provisional application Ser. No. 61/334,767, filed May 14, 2010; U.S. Provisional application Ser. No. 61/334,775, filed May 14, 2010; U.S. Provisional application Ser. No. 61/334,781, filed May 14, 2010; and U.S. Provisional application Ser. No. 61/334,787, filed May 14, 2010.

FIELD

This invention relates to iridium-containing catalysts, their production and use.

BACKGROUND

Iridium, like other elements of Group VIII of the Periodic Table, is known to be active for hydrogenation/dehydrogenation reactions and, in particular, for the carbon-carbon bond scission reactions involved in ring opening of cyclic hydrocarbons. For example, U.S. Pat. No. 7,579,511 lists iridium as one suitable Group VIII metal for catalyzing the ring opening conversion of methylcyclopentane produced as a by-product of the hydroalkylation of benzene to cyclohexylbenzene.

In view of its scarcity and high cost, any commercial application of iridium as a catalyst requires that utilization of the iridium is maximized, or in other words that the iridium is effectively and uniformly dispersed on its catalytic support in a thermally stable manner. However, few studies have focused on producing highly dispersed, stable supported iridium catalysts, particularly on non-acidic supports such as silica.

For example, US Published Patent Application No. 2006/0166809 discloses a process for the manufacture of a catalyst comprising a catalytically active metal dispersed on a support, which process comprises a) treating a porous support with a compound or salt of the metal and a organic compound selected from (i) amino acids and (ii) compounds containing both an amino group and an alcohol group, to form the organic metal complex on the support; b) partially decomposing the organic metal complex on the support to the extent that the partially decomposed product (I) retains between 10 and 95% by weight of the dry weight attributed to the organic complex prior to partial decomposition, and (II) exhibits one or more infra-red absorption bands between 2100-2200 $cm^{-1}$ that are not present in the organic complex before partial decomposition; and converting the partially decomposed organic metal complex into catalytically active metal. However, although the '809 application lists iridium as one of about forty suitable catalytically active metals, the Examples focus on the production of ruthenium catalysts via reaction of a nitrate salt. In contrast, no nitrate salt is available with iridium.

According to the present invention, it has now been found that a silica-supported iridium catalyst with excellent dispersion and nanoscale homogeneity can be prepared by modifying the partial decomposition process described in the '809 application. The resultant iridium catalyst exhibits higher hydrogen chemisorption uptakes and activity for carbon-carbon bond hydrogenolysis than conventional iridium catalysts.

SUMMARY

In one aspect, the invention resides in a process for producing a catalyst composition comprising an iridium component dispersed on a support, the process comprising:
a) treating a silica-containing support with an iridium compound and a organic compound comprising an amino group to form an organic iridium complex on the support;
b) heating the treated support in an oxidizing atmosphere at a temperature of about 325° C. to about 450° C. to partially decompose the organic metal complex on the support; and then
c) heating the treated support in a reducing atmosphere at a temperature of about 350° C. to about 500° C. to convert the partially decomposed organic iridium complex into the iridium component.

In one embodiment, the partially decomposed product retains between 10 and 95% by weight of the dry weight attributed to the organic complex prior to partial decomposition.

In one embodiment, the partially decomposed product exhibits one or more infra-red absorption bands between 2100-2200 $cm^{-1}$ that are not present in the organic complex before partial decomposition.

Conveniently, the organic compound comprises an aliphatic amine containing one or more hydroxyl groups, such as a mono-, di-, or tri-, substituted aliphatic hydroxyalkylamine, especially triethanolamine.

Alternatively, the organic compound comprises an amino acid, such as arginine.

Conveniently, heating step (b) comprises heating the treated support to a temperature of about 375° C. to about 425° C.

Conveniently, the reducing atmosphere in heating step (c) is selected from a source of hydrogen, a source of CO, and mixtures thereof.

In further aspects, the invention resides in a silica-supported iridium catalyst composition produced by the process described herein and in the use of the resultant catalyst composition in converting a cyclic aliphatic hydrocarbon to an acyclic alkane and/or alkene.

DETAILED DESCRIPTION

Figure 1:
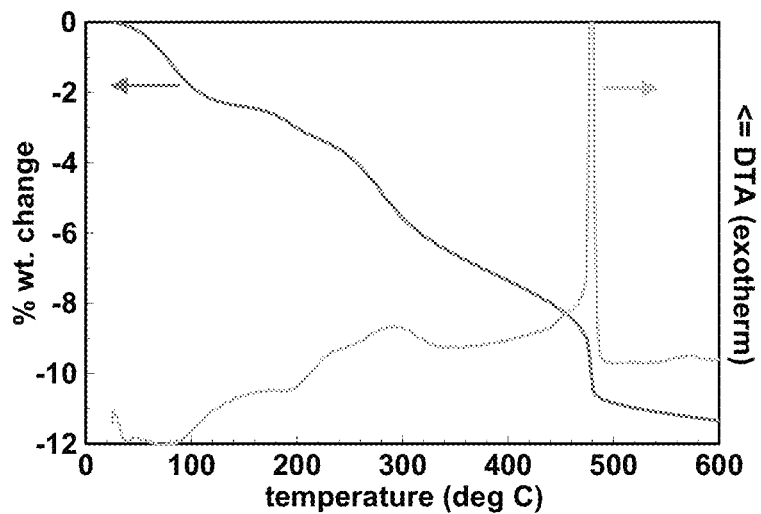
FIG. 1 is a graph of the DTA-TGA (Differential Thermal Analysis and Thermal Gravimetry Analysis) for the dried 1 wt % Ir (arginine)/$SiO_2$ catalyst precursor of Example 2 when heated in air according to Example 3. For the DTA-TGA graph, the percentage weight change of the catalyst sample is plotted against temperature to yield a Thermal Gravimetry Analysis (TGA) spectrum and the temperature difference between the sample and an inert reference are plotted against temperature yielding a Differential Thermal Analysis (DTA) spectrum.

This invention relates to a process for producing a silica-supported iridium catalyst with improved dispersion of the iridium component and to use of the resultant catalyst in converting a cyclic aliphatic hydrocarbon, especially methylcyclopentane, to an acyclic alkane and/or alkene. The catalyst shows particular utility in reducing the level of methylcyclopentane that is inevitably produced during the hydroalkylation of benzene to cyclohexylbenzene.

The present process involves initially treating a silica-containing support with an iridium compound and a organic compound comprising an amino group to form an organic iridium complex on the support.

The silica-containing support employed in the present process may be an amorphous material, such as a silica gel, or a crystalline material, such as a microporous silicate or aluminosilicate zeolite. Alternatively, the support can be a mesoporous silicate, such as MCM-41, MCM-48, and MCM-50.

The support is treated, normally by impregnation, with a liquid composition comprising an iridium compound, normally chloroiridic acid, and at least one organic compound comprising an amino group wherein the organic compound may be selected from an amino acid or an amino alcohol or mixtures thereof. The organic compound may be dispersed or dissolved in a liquid carrier, such as water. Examples of suitable amino alcohols include aliphatic hydroxyalkylamines, such as methanolamine, di-methanolamine, tri-methanolamine, ethanolamine, di-ethanolamine, tri-ethanolamine, butanolamine, di-butanolamine, tri-butanolamine, propanolamine, di-propanolamine, dimethylethanolamine, di-isopropylethanolamine, methyldiethanolamine, dimethylamino-2-propanol and tri-propanolamine. Examples of amino acids include alanine, arginine, asparagines, aspartic acid, cysteine, cystine, 3,5-dibromotyrosine, 3,5, diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine, with arginine being preferred.

Treatment of the support with the iridium compound and the organic compound forms an organic iridium complex on the support. After drying, the treated support is then heated in an oxidizing atmosphere, such as air, at a temperature of about 325° C. to about 450° C., such as about 375° C. to about 425° C., to partially, but not completely, decompose the organic metal complex on the support. The heating is typically conducted for a period of about 1 hour to about 4 hours such that the partially decomposed product retains between 10 and 95% by weight of the dry weight attributed to the organic complex prior to partial decomposition. The partially decomposed product typically exhibits one or more infra-red absorption bands between 2100-2200 cm$^{-1}$ that are not present in the organic complex before partial decomposition.

After air calcination, the treated support is heated in an reducing atmosphere at a temperature of about 350° C. to about 500° C., such as about 400° C. to about 450° C., to convert the partially decomposed organic metal complex into finely dispersed iridium particles on the silica support. Generally, the reduction is conducted for a period of about 1.5 hours to about 4 hours. Suitable reducing atmospheres comprise a source of hydrogen, a source of CO, and mixtures thereof.

The resultant catalyst is found to be effective in the ring-opening conversion of cyclic aliphatic hydrocarbons, especially methylcyclopentane, to acyclic alkanes and/or alkenes. This reaction is important since, for example, methylcyclopentane is a significant by-product in the hydroalkylation of benzene to cyclohexylbenzene, such as described in U.S. Pat. No. 7,579,511 incorporated herein by reference. Moreover, since methylcyclopentane has a similar boiling point to benzene, it cannot be readily removed from the unreacted benzene by distillation and so, without removal, will tend to build up in the benzene recycle stream. Conversion of the methylcyclopentane to methylpentane and/or methylpentene over the iridium catalyst described herein provides an attractive solution to this problem. Suitable conditions for such a ring opening reaction comprise a temperature between about 250° C. and about 400° C. and a pressure between about 100 and about 1000 kPa.

Also described herein is a process for dehydrogenating and ring opening a hydrocarbon stream comprising at least one non-aromatic six-membered ring compound and at least one non-aromatic five-membered ring compound and optionally comprising at least one aromatic compound, such as benzene. The process comprises producing a first reaction product comprising the step of contacting at least a portion of the hydrocarbon stream with a first catalyst under conditions effective to convert at least a portion of the at least one five-membered ring compound to at least one paraffin and producing a second reaction product comprising the step of contacting at least a portion of the at least one six-membered ring compound with a second catalyst under conditions effective to convert at least a portion of the at least one six-membered ring compound to at least one aromatic compound such as benzene.

In one embodiment, the hydrocarbon stream comprises at least 10 wt % benzene, at least 20 wt % benzene, at least 30 wt % benzene, at least 40 wt % benzene, at least 50 wt % benzene, at least 60 wt % benzene, at least 70 wt % benzene, and at least 80 wt % benzene. In another embodiment, the hydrocarbon stream comprises at least 1 wt % cyclohexane, at least 5 wt % cyclohexane, at least 10 wt % cyclohexane, and at least 20 wt % cyclohexane. In still another embodiment, the hydrocarbon stream comprises at least 0.05 wt % methylcyclopentane, at least 0.5 wt % methylcyclopentane, and 5 wt % methylcyclopentane.

The first catalyst employed in this process comprises an iridium-containing catalyst comprising an iridium component dispersed on a support wherein the iridium catalyst is prepared by the method described herein.

The second catalyst employed in the present process comprises at least one metal component and at least one support. The term "metal component" is used herein to include elemental metal and a metal compound that may not be purely the elemental metal, but could, for example, be at least partly in another form, such as an oxide, hydride or sulfide form. The weight % (wt %) of the metal component is herein defined as being measured as the metal present based on the total weight of the catalyst composition irrespective of the form in which the metal component is present.

Suitable metal components for use in the second catalyst comprise metals from Groups 6 to 10 of the Periodic Table of the Elements, especially platinum, palladium, ruthenium, nickel, zinc, tin, cobalt and mixtures thereof. As used herein, the numbering scheme for the Periodic Table Groups is as disclosed in Chemical and Engineering News, 63(5), p. 27 (1985).

The second catalyst employed herein has an alpha value less than 10, less than 5, and from about 0 to about 3. The alpha value is a measure of the acidic functionality of the catalyst and is described together with details of its measurement in U.S. Pat. No. 4,106,218 and in J. Catalysis, Vol. VI, pp. 278-287 (1966) and reference is made to these for such details. Higher alpha values correspond with a more active cracking catalyst. Where necessary the alpha value of the catalyst can be adjusted by methods known in the art, for example by steaming.

Preferably, the alpha value for the second catalyst is less than about 10 or less than about 5. In other embodiments, the alpha value lower limit may be about 0, about 0.1, about 0.2, about 0.3, about 0.4, about 0.5, about 0.6, about 0.7, about 0.8, about 0.9, about 1, about 2, about 3, about 4, and about 5; and the upper alpha value limit may be about 10, about 9, about 8, about 7, about 6, about 5, about 4, about 3 and about 2 with ranges from any lower limit to any upper limit being contemplated.

Conveniently, the support employed in the second catalyst is selected from the group consisting of silica, alumina, a silicate, an molecular sieve, zirconia, carbon, and carbon nanotubes, and preferably comprises silica. Additionally, the molecular sieve may be selected from aluminosilicate, an aluminophosphate, a silicoaluminophosphate, or a combination thereof. Impurities which can be present in the catalyst support (e.g., silica) are, for example, sodium salts such as sodium silicate which can be present from anywhere from 0.01 to 2 wt %.

In one embodiment, the second catalyst comprises a silica support having pore volumes and median pore diameters determined by the method of mercury intrusion porosimetry described by ASTM Standard Test D4284. The silica support may have surface areas as measured by ASTM D3663. In one embodiment, the pore volumes are in the range of from about 0.2 cc/gram to about 3.0 cc/gram. The median pore diameters are in the range from about 10 angstroms to about 2000 angstroms or from 20 angstroms to 500 angstroms; and the surface areas (m2/gram) are in the range from 10 to 1000 m2/gram or from 20 to 500 m2/gram. The support may or may not comprise a binder.

In one embodiment, the second catalyst comprises at least two metal components: (i) a metal promoter, and (ii) a dehydrogenation metal. The metal promoter comprises at least one metal component selected from Group 1 and Group 2 of the Periodic Table of Elements, such that the metal promoter may comprise any combination or mixture of metal components selected from Groups 1 and 2 of the Periodic Table of Elements. Typically, the metal promoter is present in an amount of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, and at least 1.0 wt %. In one embodiment, the metal promoter comprises at least one metal component selected from Group 1 of the Periodic Table of Elements, such as potassium, cesium and rubidium; preferably potassium and potassium compounds. In another embodiment, the metal promoter comprises at least one metal component selected from Group 1 of the Periodic Table of Elements. In still another embodiment, the metal promoter comprises at least one metal component selected from Group 2 of the Periodic Table of Elements such as beryllium, calcium, magnesium, strontium, barium and radium; preferably calcium and magnesium. Typically, the metal promoter is present in an amount between about 0.1 and about 5 wt % of the catalyst or between about 0.2 and about 4 wt % of the catalyst or between about 0.3 and about 3 wt % of the catalyst.

In addition, the second catalyst comprises a dehydrogenation component comprising at least one metal component selected from Groups 6 to 10 of the Periodic Table of Elements, such as platinum and palladium such that the dehydrogenation component may comprise any combination or mixture of metal components selected from Groups 6 to 10 of the Periodic Table of Elements. In another embodiment, the dehydrogenation component comprises at least one metal component selected from Group 10 of the Periodic Table of Elements.

Typically, the dehydrogenation component is present in an amount between about 0.1 and about 10 wt % of the catalyst such as between about 0.1 and about 5 wt % of the catalyst or between about 0.2 and about 4 wt % of the catalyst or between about 0.3 and about 3 wt % of the catalyst. In another embodiment, the metal promoter is present in an amount of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, and at least 1.0 wt %.

The second catalyst is produced by initially treating the support, such as by impregnation, with a solution of the metal promoter, such as an aqueous solution of potassium carbonate. After drying, the treated support is calcined, normally in an oxygen-containing atmosphere, such as air, at a temperature of about 100° C. to about 700° C. for a time of about 0.5 to about 50 hours. The calcined support is then treated, again typically by impregnation, with a solution of the dehydrogenation component or a precursor thereof.

In another embodiment, the dehydrogenation component may be impregnated into the support with the aid of at least one organic dispersant. The organic dispersant may help to increase the metal dispersion of the metal promoter. The at least one organic dispersant may be used to increase the metal dispersion of the dehydrogenation component with or without the impregnation of the metal promoter into the support. The at least one organic dispersant is selected from an amino alcohol and an amino acid, such as arginine. Generally, the organic dispersant is present in an amount between about 1 and about 20 wt % of the solution.

After treatment with the dehydrogenation component, the support is again dried and calcined, normally in an oxygen-containing atmosphere, such as air, at a temperature of about 100° C. to about 600° C. for a time of about 0.5 to about 50 hours.

In an alternative embodiment, the dehydrogenation catalyst is produced by initially treating the support, such as by impregnation, with a solution containing both the metal promoter and the dehydrogenation component or a precursor thereof, optionally together with at least one organic dispersant selected from an amino alcohol and an amino acid, such as arginine. In this case, after drying, a single calcination procedure, normally in an oxygen-containing atmosphere, such as air, at a temperature of about 100° C. to about 700° C. for a time of about 0.5 to about 50 hours, is used to produce the finished catalyst.

The first reaction product will be produced in a first reaction zone comprising the first catalyst and the second reaction product will be produced in a second reaction zone comprising the second catalyst. In one embodiment, the different reaction zones may be contained within the same reactor vessel such as a stacked bed configuration. In another embodiment, the first and second catalyst may be contained in separate reactor vessels.

The first reaction zone is generally operated at a temperature between about 200° C. and about 750° C., such as between about 300° C. and about 500° C., a pressure between about 100 and about 7,000 kPaa, such as between about 300 and about 3000 kPaa, a weight hourly space velocity (WHSV) between about 0.2 and about 50 $hr^{-1}$, such as between about 1 and about 20 $hr^{-1}$ and a hydrogen to hydrocarbon feed molar ratio between about 0.1 and about 20, such as between about 1 and about 5.

It is preferable to operate the first reaction zone at a temperature between about 100° C. and about 400° C., a pressure between about 100 and about 7,000 kPaa, and a hydrogen to hydrocarbon molar ratio between about 0.1 to about 10.

Preferably, the temperature of the first reaction zone is from about 300° C. to about 750° C.; from about 350° C. to about 650° C.; from about 400° C. to about 550° C., from about 450° C. to about 550° C., and from about 400° C. to about 500° C. In other embodiments, the temperature lower limit may be about 350° C., about 400° C., about 430° C., about 440° C., about 450° C., about 460° C., about 470° C., about 480° C., and about 490° C.; and the upper limit temperature may be about 500° C., about 510° C., about 520° C., about 530° C., about 540° C., about 550° C., about 600° C., about 650° C., about 700° C., and about 750° C. with ranges from any lower limit to any upper limit being contemplated. In still other embodiments, the temperature lower limit may be about 500° C., about 510° C., about 520° C., about 530° C., about 540° C., and about 550° C.; and the upper limit temperature may be about 560° C., about 570° C., about 580° C., about 590° C., about 600° C., about 650° C., about 700° C., and about 750° C. with ranges from any lower limit to any upper limit being contemplated.

Preferably, the pressure of the first reaction zone is from 0 to about 300 psig (0 to 2068 kPag), 50 to 300 psig (345 to 2068 kPag), from 60 to 300 psig (414 to 2068 kPag), from 70 to 300 psig (482 to 2068 kPag), from 80 to 300 psig (552 to 2068 kPag), from 90 to 300 psig (621 to 2068 kPag), and from 100 to 300 psig (689 to 2068 kPag). In other embodiments, the temperature lower limit may be 50 psig (345 kPag), 60 psig (414 kPag), 70 psig (482 kPag), 80 psig (552 kPag), 90 psig (621 kPa), and 100 psig (689 kPag); and the upper limit temperature may be 125 psig (862 kPag), 150 psig (1034 kPag), 175 psig (1207 kPag), 200 psig (1379 kPag), 250 psig (1724 kPag), 300 psig (2068 kPag), 400 psig (2758 kPag), and 500 psig (3447 kPag) with ranges from any lower limit to any upper limit being contemplated. In still other embodiments, the temperature lower limit may be 150 psig (1034 kPag), 160 psig (1103 kPag), 170 psig (1172 kPag), 180 psig (1241 kPag), 190 psig (1310 kPag), and 200 psig (1379 kPag); and the upper limit temperature may be 250 psig (1724 kPag), 300 psig (2068 kPag), 400 psig (2758 kPag), and 500 psig (3447 kPag) with ranges from any lower limit to any upper limit being contemplated.

The second reaction zone may be operated at about the same conditions as the first reaction zone but preferably is operated at a temperature between about 250° C. and about 650° C., a pressure between about 100 and about 7,000 kPaa, and a hydrogen to hydrocarbon molar ratio between about 0.1 to about 10. This is generally true when stacked bed process is utilized; however, the operating conditions can fluctuate between the first and second beds regardless of the configuration. In the separate reactor embodiment, the conditions will be within the same range of the first reaction zone, but may be different from the first reaction zone conditions.

Although the present process can be used with any hydrocarbon stream comprising at least one non-aromatic six-membered ring compound and at least one non-aromatic five-membered ring compound, the process has particular application as part of an integrated process for the conversion of benzene to phenol. In such an integrated process the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

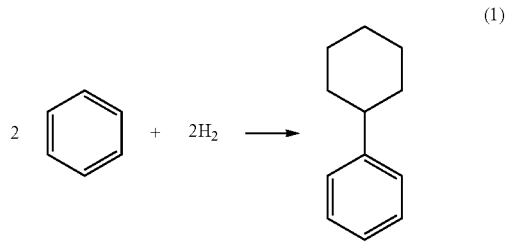 [SMILES: c1ccccc1 ; c1ccc(C2CCCCC2)cc1]

(1)

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is generally a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example, from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example, at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), p. 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain unreacted benzene feed, some dialkylated products, and other by-products, particularly cyclohexane, and methylcyclopentane. In fact, typical selectivities to cyclohexane and methylcyclopentane in the hydroalkylation reaction are 1-25 wt % and 0.1-2 wt % respectively. The hydroalkylation reaction effluent is therefore fed to a separation system normally comprising at least two distillation towers. Given the similar boiling points of benzene, cyclohexane, and methylcyclopentane, it is difficult to separate these materials by distillation. Thus, in a distillation tower, a $C_6$-rich stream comprising benzene, cyclohexane, and methylcyclopentane is recovered from the hydroalkylation reaction effluent. This $C_6$-rich stream is then subjected to the dehydrogenation process described above such that at least a portion of the cyclohexane in the stream is converted to benzene and at least a portion of the methylcyclopentane is converted to linear and/or branched paraffins, such as 2-methylpentane, 3-methylpentane, n-hexane, and other hydrocarbon components such as isohexane, $C_5$ aliphatics, and $C_1$ to $C_4$ aliphatics. The dehydrogenation product stream is then fed to a further separation system, typically a further distillation tower, to divide the dehydrogenation product stream into a $C_6$ recycle stream and a paraffin-rich stream comprising 2-methylpentane, 3-methylpentane, and other $C_1$ to $C_6$ paraffins. The $C_6$ recycle stream can then be recycled to the hydroalkylation step, while the paraffinic stream can be used as a fuel for the process.

After separation of the $C_6$-rich stream, the remainder of hydroalkylation reaction effluent is fed a second distillation tower to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, including large pore molecular sieves such as a molecular sieve of the MCM-22 family, zeolite beta, MCM-68 (see U.S. Pat. No. 6,014,018), zeolite Y, zeolite USY, and mordenite. A large pore molecular sieve has an average pore size in excess of 7 Å in some embodiments or from 7 Å to 12 Å in other embodiments. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1. The transalkylation reaction effluent can then be returned to the second distillation tower to recover the additional monocyclohexylbenzene product produced in the transalkylation reaction.

After separation in the second distillation tower, the cyclohexylbenzene is converted into phenol by a process similar to the Hock process. In this process, the cyclohexylbenzene is initially oxidized to the corresponding hydroperoxide. This is accomplished by introducing an oxygen-containing gas, such as air, into a liquid phase containing the cyclohexylbenzene. Unlike the Hock process, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo [2.2.1]hept-5-ene-2,3-dicarboximide, N-hydroxy-cis-cyclohexane-1,2-dicarboximide, N-hydroxy-cis-4-cyclohexene-1,2dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The effluent from the cleavage reaction comprises phenol and cyclohexanone in substantially equimolar amounts and, depending on demand, the cyclohexanone can be sold or can be dehydrogenated into additional phenol. Any suitable dehydrogenation catalyst for the dehydrogenation of cyclohexanone can be used in this reaction.

Preferably, the cyclohexanone dehydrogenation catalyst is selected from the catalyst compositions described as being useful for the second catalyst in the first conversion step of this invention.

Suitable conditions for the dehydrogenation step comprise a temperature of about 250° C. to about 700° C. and a pressure of about 0.01 atm to about 20 atm (1 kPa to 2000 kPa), such as a temperature of about 300° C. to about 450° C. and a pressure of about 1 atm to about 10 atm (100 kPa to 1000 kPa).

When a stream is described as being "rich" in a specified species, it is meant that the specified species in that stream is enriched relative to other species in the same stream or composition on a weight percentage basis. For illustration purposes only, a cyclohexylbenzene-rich stream will have a cyclohexylbenzene wt % greater than any other species or component in that same stream. A "$C_6$" species generally means any species containing 6 carbon atoms.

The invention will now be more particularly described with reference to the following Examples and the accompanying drawings.

In the Examples, hydrogen chemisorption measurements were obtained under static high vacuum conditions on a Quantachrome Autosorb 1A instrument. Approximately 0.4 g of catalyst were reduced in flowing hydrogen and heated at 2° C./min to the final reduction temperature and held at that temperature for 2 hours. Following reduction, the sample was evacuated (while still at the reduction temperature) with a turbomolecular pump for 30 minutes to remove any chemisorbed hydrogen. With the sample still under vacuum, the temperature was lowered to 40° C. and held isothermal during subsequent treatments. An 8-point isotherm (with pressures between 80 and 400 torr) was measured at 40° C. with $H_2$ as the adsorbent molecule. Extrapolation of the linear portion of this curve to zero pressure gives the total or combined adsorption uptake. The sample was then evacuated (at 40° C.) to remove the weakly chemisorbed hydrogen and the weak (or backsorption) isotherm measured. Subtraction of the two isotherms yields the strong (or difference) isotherm. We have found that sizes extrapolated from the difference isotherm (strong chemisorption) with a stoichiometry of 2H per Ir best approximates the TEM (transmission electron micrograph)-measured value.

DTA spectra were obtained using approximately 150 mg of catalyst loaded into a Mettler TGA 851 thermal balance. The catalysts were treated under flowing air (50 cc/min) at one atmosphere total pressure. The samples were heated at 4° C./min from room temperature to the final temperature. Heat effects were measured by an integrated thermopile to assess the relative strength of the endothermic and exothermic events.

EXAMPLE 1 (Comparative)

Preparation of 1 Wt % (Weight %) $Ir/SiO_2$ 1.09 g of a chloroiridic acid stock solution of 18.5 wt % Ir content was dissolved and diluted with water to a total volume of 22 cc. The acid solution was impregnated by incipient wetness onto 20 g of Davison 646 silica support, which has a surface area of 300 $m^2/g$, an average pore diameter of 150 A, a 35-60 mesh size, and an incipient wetness pore volume of 1.1 cc/g. After impregnation, the sample was dried overnight at 100° C. to give a 1 wt % $Ir/SiO_2$ catalyst. A portion of the dried catalyst was then calcined for 4 hours at 350° C. and another portion calcined for 4 hours at 500° C. In both cases a ramp rate of 2° C./minute was used to reach the desired calcination temperature.

EXAMPLE 2

Preparation of 1 Wt % Ir (Arginine)/$SiO_2$

An arginine-containing catalyst was prepared by dissolving 1.09 g of a chloroiridic acid stock solution of 18.5 wt % Ir content along with 1.465 g of arginine into water to a total volume of 22 cc. The resultant solution had an arginine to Ir mole ratio of 8:1 and was impregnated by incipient wetness onto 20 grams of Davison 646 silica support. After impregnation, the sample was dried overnight at 100° C. to give an arginine-containing 1 wt % $Ir/SiO_2$ catalyst. A portion of the dried catalyst was then calcined for 4 hours at 400° C. and another portion calcined for 4 hours at 500° C. A ramp rate of 2° C./minute was used to reach the desired calcination temperature.

EXAMPLE 3

DTA Testing of 1 Wt % Ir (Arginine)/$SiO_2$

A portion of the dried arginine-containing 1 wt % $Ir/SiO_2$ sample of Example 2 was heated in air to 600° C. at 4° C./min. The DTA-TGA (Differential Thermal Analysis and Thermal Gravimetry Analysis) plot is shown in FIG. 1. Several weak exotherms are shown at temperatures lower than 400° C. and then a very sharp and strong exotherm at about 475° C.

EXAMPLE 4

DTA Testing of 1 Wt % Ir (Arginine)/$SiO_2$ after Calcination at 400° C.

Figure 2:
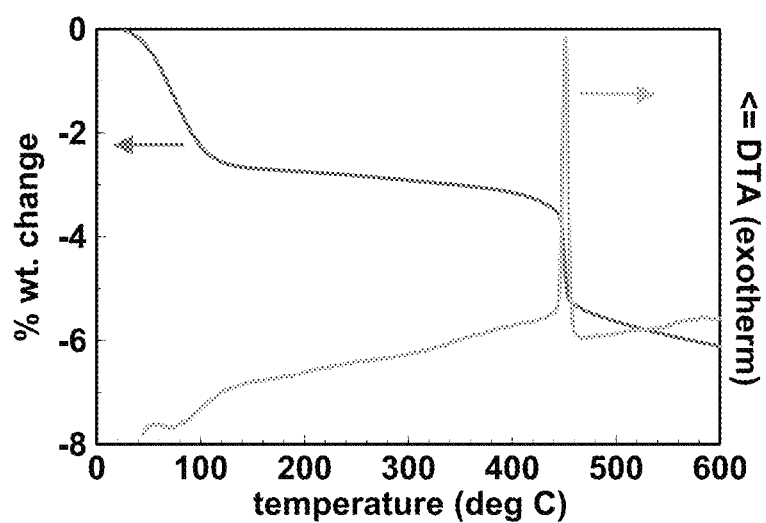
FIG. 2 is a graph of percentage weight change against temperature and a DTA spectrum for the dried and calcined (at 400° C.) 1 wt % Ir(arginine)/SiO$_2$ catalyst precursor of Example 2 when heated in air according to Example 4.

A portion of the arginine-containing 1 wt % $Ir/SiO_2$ sample of Example 2 that had been calcined at 400° C. was heated in air to 600° C. at 4° C./min. The DTA-TGA plot is shown in FIG. 2, which shows a single strong exotherm still exists indicating that the complex formed after partial decomposition of the impregnate is intact after the 400° C. calcination.

EXAMPLE 5

$H_2$ Reduction of 1 Wt % Ir (Arginine)/$SiO_2$ after Calcination at 400° C.

Figure 3:
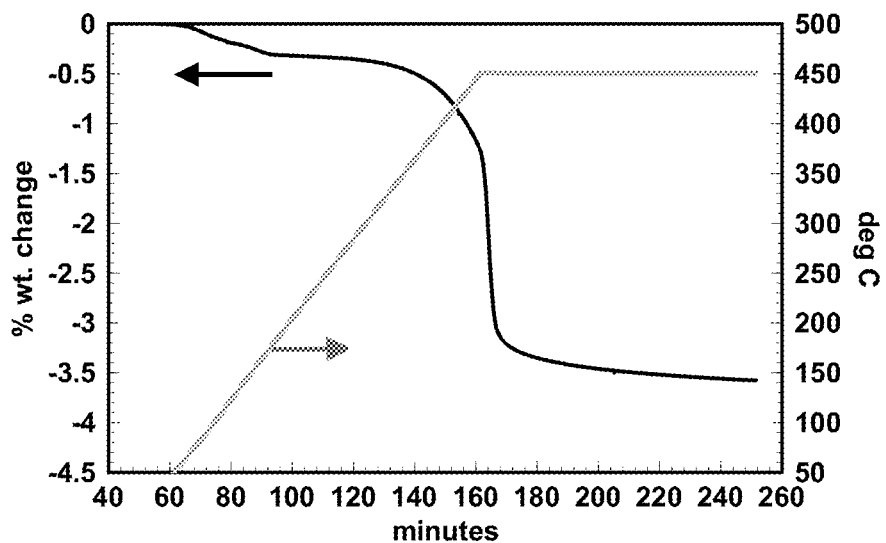
FIG. 3 is a graph of temperature and percentage weight change against time on stream for the dried and calcined (at 400° C.) 1 wt % Ir(arginine)/SiO$_2$ catalyst precursor of Example 2 when reduced in 100% H$_2$ according to Example 5.

A portion of the arginine-containing 1 wt % $Ir/SiO_2$ sample of Example 2 that had been calcined at 400° C. was reduced in hydrogen in the TGA instrument at one atmosphere pressure and with 100% $H_2$ gas flowing at 125 cc/min. The reduction profile is given in FIG. 3 and shows that reduction starts near 350° C. and requires temperatures of 400-450° C. to fully reduce the sample.

EXAMPLE 6

DTA Testing of 1% $Ir/SiO_2$

A portion of the dried 1 wt % $Ir/SiO_2$ sample of Example 1 was heated in air to 600° C. at 4° C./min. The TG/DTA plot is given in FIG. 4 and shows the (endothermic) water loss at low temperature and then the decomposition of the chloroiridate complex at temperatures above 420° C. (with a very weak exotherm) to form iridium oxide.

EXAMPLE 7

Chemisorption Testing of 1 Wt % $Ir/SiO_2$

The hydrogen chemisorption uptakes (strong uptake from dual isotherms) of the dried and calcined 1 wt % $Ir/SiO_2$ samples of Example 1 were measured at 40° C. as a function of reduction temperature. The values are shown in Table 1.

TABLE 1

| Thermal Treatment (° C. in air) | Reduction Temp (° C.) | $H_2/Ir \times 100$ |
|---|---|---|
| 100 | 200 | 20.9 |
| 100 | 250 | 25.0 |
| 100 | 325 | 31.1 |
| 100 | 400 | 33.8 |
| 350 | 250 | 20.4 |
| 350 | 325 | 24.8 |
| 350 | 400 | 27.3 |
| 500 | 400 | 3.3 |

Figure 4:
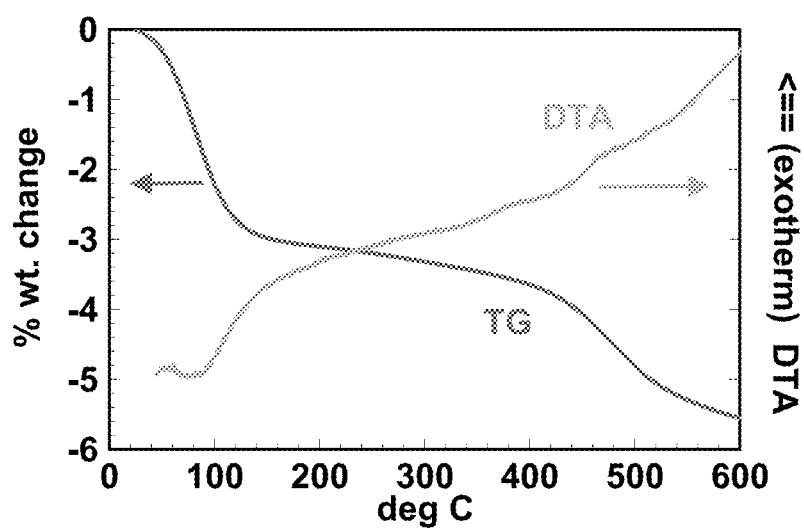
FIG. 4 is a graph of percentage weight change against temperature and a DTA spectrum for the dried 1 wt % Ir/SiO$_2$ catalyst precursor of Example 1 when heated in air according to Example 5.

The data in Table 1 show that the hydrogen chemisorption values are relatively low and do not substantially change with calcinations at 100° C. or 350° C. As seen in FIG. 4, after the chloroiridate complex decomposes to form $IrO_2$ at temperatures of about 450° C., the hydrogen chemisorption number (post 500° C. calcination) is very low. Table 1 also shows that reduction of the Example 1 samples occurs between 325 and 400° C.

EXAMPLE 8

Chemisorption Testing of 1 Wt % Ir(Arginine)/SiO$_2$

The hydrogen chemisorption uptakes (strong uptake from dual isotherms) of the calcined 1 wt % Ir(arginine)/SiO$_2$ samples of Example 2 were measured at 40° C. as a function of reduction temperature. The values are shown in Table 2.

TABLE 2

| Thermal Treatment (° C. in air) | Reduction Temp (° C.) | H$_2$/Ir × 100 |
| --- | --- | --- |
| 400 | 200 | 0 |
| 400 | 250 | 0 |
| 400 | 325 | 0 |
| 400 | 400 | 74.9 |
| 400 | 450 | 69.1 |
| 500 | 400 | 5.9 |

Table 2 shows that there after the 400° C. calcinations of the arginine-containing complex of Example 2, a reduction temperature of 400° C. is required to reduce the complex and obtain metal sites. The high hydrogen chemisorption values after 400 and 450° C. reduction greatly exceed those obtained with the arginine-free samples of Example 1. After 500° C. calcination, the complex fully oxidizes and the iridium oxide that forms is mobile and on reduction forms large particles (low dispersion values).

EXAMPLE 9

Preparation and Testing of 1% Wt Ru(Arginine)/SiO$_2$

A 1 wt % Ru(arginine)/SiO$_2$ catalyst was prepared in an analogous way to the 1 wt % Ir(arginine)/SiO$_2$ catalyst of Example 2. To 13.46 g of an aqueous ruthenium nitrosyl nitrate solution containing 1.5 wt % Ru were added 2.78 g arginine (arginine/Ru molar ratio of 8:1) and enough water to bring the total volume to 22 cc. The solution was impregnated by incipient wetness onto 20 grams of Davison 646 silica, and dried overnight at 100° C. One portion of the catalyst was heated in air at 4° C./min to 300° C. and held for one hour, a second portion was heated to 325° C. and held one hour and a third portion was heated to 400° C. in air and held at that temperature for one hour. The hydrogen chemisorption values of the samples were measured after 400° C. reduction and the results are shown in Table 3.

TABLE 3

| Sample | Thermal Treatment (° C. in air) | Reduction Temp (° C.) | |
| --- | --- | --- | --- |
| | | | H$_2$/Ir* × 100 |
| 1 wt % Ir (arginine)/ SiO$_2$ | 400 | 325 | 0 |
| | 400 | 400 | 74.9 |
| | 400 | 450 | 69.1 |
| | | | H$_2$/Ru* × 100 |
| 1 wt % Ru(arginine)/ SiO$_2$ | 300 | 400 | 77.8 |
| | 325 | 400 | 1.5 |
| | 400 | 400 | 2.2 |

*For supported Ru, the single isotherm is used to estimate particle size and the hydrogen chemisorption stoichiometry is H/Ru of 1/1. For Ir the dual isotherm is used and the hydrogen chemisorption stoichiometry is H/Ru of 2/1.

Note that for the 1 wt % Ru(arginine)/SiO$_2$ sample the high hydrogen chemisorption value obtained after a 300° C. calcination has become very low after a 325° C. or 400° C. calcination, apparently due to the decomposition of the Ru complex at much lower temperatures than the Ir complex. It is surprising that the optimum calcination temperature to partially decompose the Ir impregnate is substantially higher than that of the Ru impregnate.

EXAMPLE 10

Preparation and Testing of 1% Ir(Triethanolamine)/SiO$_2$

A sample of 1% Ir/SiO2 with triethanolamine (TEA) rather than arginine added to the impregnation solution was prepared. This TEA-containing catalyst was prepared by dissolving 1.09 g of a chloroiridic acid stock solution of 18.5% Ir content along with 1.26 g of TEA into water to a total volume of 22 cc. This was impregnated by incipient wetness onto 20 g of Davison 646, and then dried overnight at 100° C. A portion of this catalyst was calcined at 400° C. for 4 hours using a ramp rate of 2° C./minute to reach the desired calcination temperature. The hydrogen chemisorption values were measured and are shown in Table 4.

TABLE 4

| Thermal Treatment (° C. in air) | Reduction Temp (° C.) | H2/Ir × 100 |
| --- | --- | --- |
| 400 | 325 | 75.5 |
| 400 | 400 | 79.6 |
| 400 | 450 | 77.4 |

This example shows that the aminoalcohol, triethanolamine, is as effective as the amino acid, arginine, when used to prepare an impregnate that is then partially decomposed to the complex, which is then reduced to form small metal particles.

EXAMPLE 11

Catalyst Testing in Ring Opening of Methylcyclopentane

The following catalysts were compared in the ring opening of methylcyclopentane:
(1) dried 1 wt % Ir/SiO$_2$ of Example 1;
(2) 1 wt % ft/SiO$_2$ of Example 1 after calcination at 500° C.;
(3) 1 wt % ft(arginine)/SiO$_2$ catalyst of Example 2 after calcination at 400° C.; and
(4) 1 wt % ft(arginine)/SiO$_2$ catalyst of Example 2 after calcination at 500° C.

Each catalyst was sized to 14-30 mesh particles and 0.5 to 2.0 g of the sized catalyst was diluted with 40-60 mesh quartz chips to 3 cc. The catalyst/quartz chips mixture was thoroughly mixed and loaded into an isothermal, down-flow, ⅜ inch (0.95 cm) outside diameter, fixed-bed reactor operated in a down-flow mode. The reactor was pressurized to 100 psig (791 kPa) with hydrogen flow set at 200 cc/min. The reactor was ramped up to 425° C. at 2° C./min. Once reaching 425° C., the temperature was held constant for 1 hour. The reactor was then cooled down to at 5° C./min until a stable temperature of 260° C. was achieved. The pressure of the reactor was increased to 350 psig (2514 kPa). The hydrogen flow was reduced to 96 cc/min, and methylcyclopentane was introduced by a liquid feed pump at 5.34 cc/hr. H$_2$/MCP molar ratio was 5:1. Total product analysis (except hydrogen content) was determined every 2 hours starting at 0.5 hour on stream with an HP-5890 GC. The GC was equipped with a 60 meter DB-1 column (0.25 mm internal diameter and 1 mm film thickness) and flame ionization detector. The GC temperature program was: −20° C., 2 min, 8° C./min to 250° C., and hold for 30 min. MCP conversion was measured after 0.5 hour on stream and 3 days on stream and are denoted as fresh and stabilized activities respectively. Conversion was all kept below 98%. First order kinetics were used to calculate a rate constant (k) for each sample, with $k_i$ indicating the initial value at 0.5 hour on stream and $k_s$ the value at 3 days on stream. In Table 5, the dispersions and rate constants are compared and this is also shown in FIGS. 5 and 6.

TABLE 5

| Sample Description | $H_2/Ir \times 100$ (reduced 400° C.) | $K_i$ (MCP conversion) | $K_s$ (MCP conversion) |
|---|---|---|---|
| 1 wt % Ir/SiO$_2$ dried 100° C. | 63 | 24.6 | 0.35 |
| 1 wt % Ir/SiO$_2$ calcined 500° C. | 19 | 12 | 0.14 |
| 1 wt % Ir(arginine)/SiO$_2$ calcined 400° C. | 74.9 | 27.2 | 0.86 |
| 1 wt % Ir(arginine)/SiO$_2$ calcined 500° C. | 5.9 | 5.1 | 0.18 |

Figure 5:
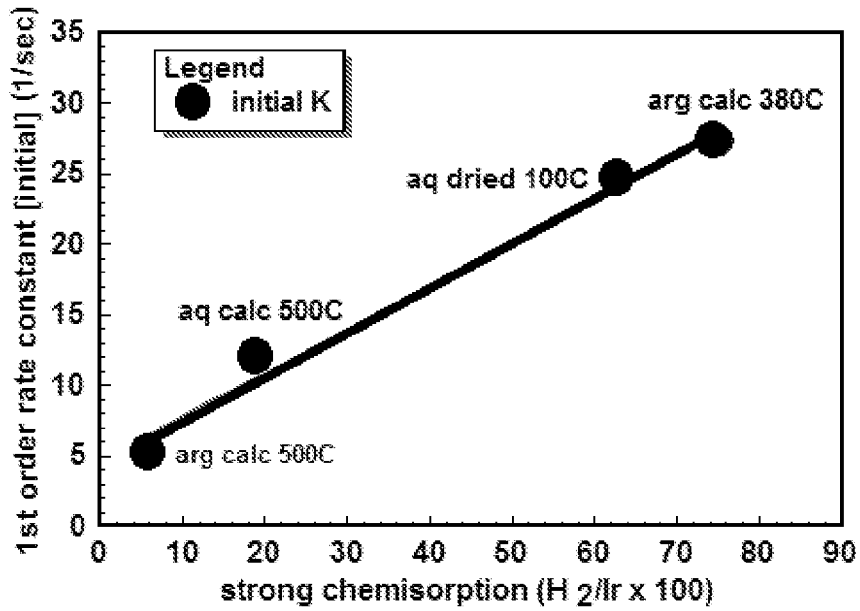
FIG. 5 is a graph of initial first-order rate constant against hydrogen chemisorption for methylcyclopentane ring-opening reactions carried out over various catalyst samples in connection with Example 11.
Figure 6:
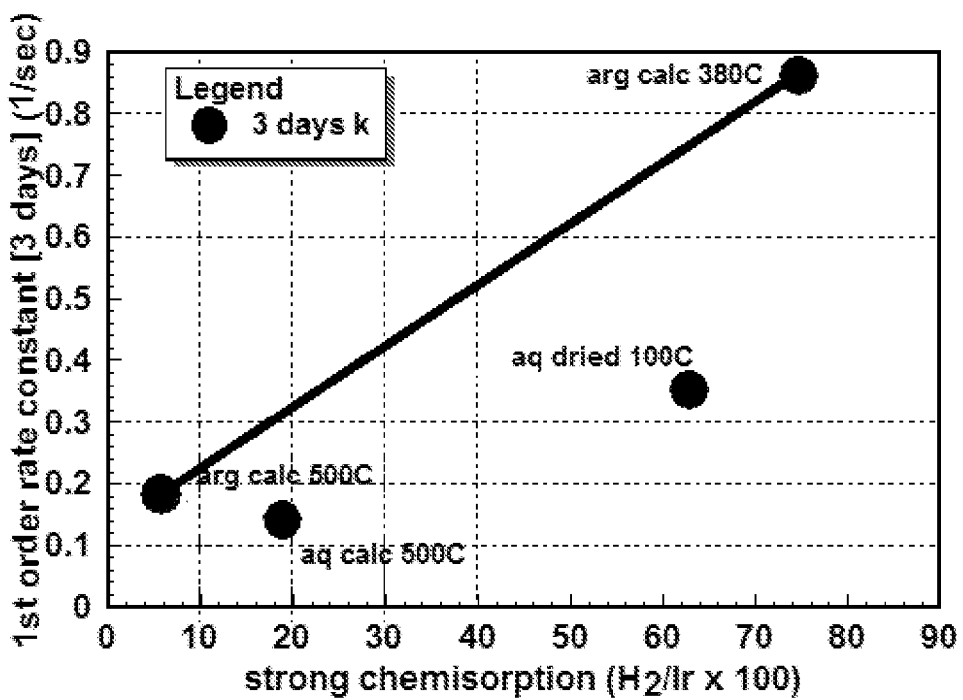
FIG. 6 is a graph of first-order rate constant (after 3 days of activity) against hydrogen chemisorption for methylcyclopentane ring-opening reactions carried out over various catalyst samples in connection with Example 11.

FIG. 5 shows that the initial activity for methylcyclopentane ring opening is a function of the number of metal sites at the particle surface as measured by hydrogen chemisorption (i.e., the dispersion×the metal loading). In particular, the 1 wt % Ir(arginine)/SiO$_2$ catalyst of Example 2 that had been calcined at 400° C. exhibited the highest ring opening activity.

FIG. 6 shows the activity data after the catalysts have been on stream for 3 days. During this time there is significant deactivation. This activity is plotted as a function of the hydrogen chemisorption of the fresh catalysts. We have placed a line through the two samples prepared with arginine. The activities of the two catalysts prepared without the addition of arginine are below this line, showing that they have deactivated more on a relative basis than the two arginine prepared catalysts, most likely because the Ir particles are more clustered together in the aqueous only preparation than in the preparation with arginine.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

In various embodiments, this invention relates to:
1. A process for producing a catalyst composition comprising an iridium component dispersed on a support, the process comprising:
    a) treating a silica-containing support with at least one iridium compound and at least one organic compound comprising an amino group to form a treated support comprising an organic iridium complex on the support;
    b) heating the treated support in an oxidizing atmosphere at a temperature of about 325° C. to about 450° C. to partially decompose the organic iridium complex on the support to form a partially decomposed organic iridium complex; and
    c) heating the treated support in an reducing atmosphere at a temperature of about 350° C. to about 500° C. to convert the partially decomposed organic iridium complex into the iridium component.
2. The process of embodiment 1, wherein the at least one organic compound is selected from an (i) amino acids and (ii) compounds comprising an amino group and an alcohol group.
3. The process of embodiment 1, wherein the partially decomposed organic iridium complex retains between 10 and 95% by weight of the dry weight attributed to the organic iridium complex prior to partial decomposition.
4. The process of embodiment 1, wherein the partially decomposed organic iridium complex exhibits one or more infrared absorption bands between 2100-2200 cm$^{-1}$ that are not present in the organic complex before partial decomposition.
5. The process of embodiment 1, wherein the organic compound comprises an aliphatic amine containing one or more hydroxyl groups.
6. The process of embodiment 1, wherein the organic compound comprises a hydroxyalkylamine
7. The process of embodiment 6, wherein the hydroxyalkylamine comprises one or more of: methanolamine, di-methanolamine, tri-methanolamine, ethanolamine, di-ethanolamine, tri-ethanolamine, butanolamine, di-butanolamine, tri-butanolamine, propanolamine, di-propanolamine, dimethylethanolamine, di-isopropylethanolamine, methyldiethanolamine, dimethylamino-2-propanol and tri-propanolamine
8. The process of embodiment 1, wherein the organic compound comprises tri-ethanolamine
9. The process of embodiment 1, wherein the organic compound comprises an amino acid.
10. The process of embodiment 1, wherein the amino acid comprises arginine.
11. The process of embodiment 1, wherein heating step (b) comprises heating the treated support to a temperature of about 375° C. to about 425° C.
12. A catalyst composition produced by the process of embodiment 1.
13. A method for converting a cyclic aliphatic hydrocarbon to acyclic alkane or alkene comprising contacting the cyclic aliphatic hydrocarbon under ring-opening conditions with a catalyst wherein the catalyst is produced by a method comprising:
    a) treating a silica-containing support with an iridium compound and a organic compound comprising an amino group to form a treated support comprising an organic iridium complex on the support;
    b) heating the treated support in an oxidizing atmosphere at a temperature of about 325° C. to about 450° C. to partially decompose the organic iridium complex on the support to form a partially decomposed organic iridium complex; and
    c) heating the treated support in an reducing atmosphere at a temperature of about 350° C. to about 500° C. to convert the partially decomposed organic iridium complex into the iridium component.
14. The process of embodiment 13, wherein the at least one organic compound is selected from an (i) amino acids; and (ii) compounds comprising an amino group and an alcohol group.
15. The process of embodiment 13, wherein the partially decomposed organic iridium complex retains between 10 and 95% by weight of the dry weight attributed to the organic iridium complex prior to partial decomposition.

16. The process of embodiment 13, wherein the cyclic aliphatic hydrocarbon is methylcyclopentane.
17. The process of embodiment 13, wherein the partially decomposed organic iridium complex exhibits one or more infra-red absorption bands between 2100-2200 cm$^{-1}$ that are not present in the organic complex before partial decomposition.
18. The process of embodiment 13, wherein the organic compound comprises an aliphatic amine containing one or more hydroxyl groups.
19. The process of embodiment 13, wherein the organic compound comprises a substituted aliphatic hydroxyalkylamine
20. The process of embodiment 13, wherein the hydroxyalkylamine comprises one or more of: methanolamine, di-methanolamine, tri-methanolamine, ethanolamine, di-ethanolamine, tri-ethanolamine, butanolamine, di-butanolamine, tri-butanolamine, propanolamine, di-propanolamine, dimethylethanolamine, di-isopropylethanolamine, methyldiethanolamine, dimethylamino-2-propanol and tri-propanolamine
21. The process of embodiment 13, wherein the organic compound comprises tri-ethanolamine
22. The process of embodiment 13, wherein the organic compound comprises an amino acid.
23. The process of embodiment 13, wherein the amino acid comprises arginine.
24. The process of embodiment 13, wherein the heating step (b) comprises heating the treated support to a temperature of about 375° C. to about 425° C.
25. A process for producing cyclohexylbenzene, the process comprising:
   (i) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and benzene;
   (ii) separating at least a portion of the hydroalkylation reaction product stream into a C$_6$-rich stream comprising benzene, cyclohexane, and methylcyclopentane and a cyclohexylbenzene-rich stream;
   (iii) producing a first reaction product stream comprising the step of contacting at least a portion of the C$_6$-rich stream with a first catalyst comprising at least one support and at least one metal component and the contacting being conducted under conditions to convert at least a portion of the methylcyclopentane to at least one paraffin wherein the first catalyst is produced by a method comprising:
      a) treating a silica-containing support with an iridium compound and an organic compound comprising an amino group to form a treated support comprising an organic iridium complex on the support;
      b) heating the treated support in an oxidizing atmosphere at a temperature of about 325° C. to about 450° C. to partially decompose the organic iridium complex on the support to form a partially decomposed organic iridium complex; and
      c) heating the treated support in an reducing atmosphere at a temperature of about 350° C. to about 500° C. to convert the partially decomposed organic iridium complex into the iridium component;
   (iv) producing a second reaction product stream comprising the step of contacting at least a portion of the first reaction product stream with a second catalyst comprising at least one support and at least one metal component and under conditions effective to convert at least a portion of the cyclohexane to benzene;
   (v) separating at least a portion of the second reaction product stream produced in producing step (iv) into a benzene recycle stream and a paraffins-rich stream comprising 2-methylpentane and 3-methylpentane; and
   (vi) recycling at least a portion of the benzene recycle stream to the contacting step (i).
26. The process of embodiment 25, wherein the at least one organic compound is selected from an (i) amino acids and (ii) compounds comprising an amino group and an alcohol group.
27. The process of embodiment 25, wherein the partially decomposed organic iridium complex retains between 10 and 95% by weight of the dry weight attributed to the organic iridium complex prior to partial decomposition.
28. The process of embodiment 25, wherein the partially decomposed organic iridium complex exhibits one or more infra-red absorption bands between 2100-2200 cm$^{-1}$ that are not present in the organic complex before partial decomposition.
29. The process of embodiment 25, wherein the conditions in the producing step (iii) comprise a temperature between about 100° C. and about 400° C., a pressure between about 100 and about 7,000 kPaa, and a hydrogen to hydrocarbon molar ratio between about 0.1 to about 10.
30. The process of embodiment 25, wherein the conditions in the producing step (iv) comprise a temperature between about 250° C. and about 650° C., a pressure between about 100 and about 7,000 kPaa, and a hydrogen to hydrocarbon molar ratio between about 0.1 to about 10.

The invention claimed is:
1. A process for producing cyclohexylbenzene, the process comprising:
   (i) contacting benzene and hydrogen in the presence of a hydroalkylation catalyst under hydroalkylation conditions effective to form a hydroalkylation reaction product stream comprising cyclohexylbenzene, cyclohexane, methylcyclopentane, and benzene;
   (ii) separating at least a portion of the hydroalkylation reaction product stream into a C$_6$-rich stream comprising benzene, cyclohexane, and methylcyclopentane, and a cyclohexylbenzene-rich stream;
   (iii) contacting at least a portion of the C$_6$-rich stream with a first catalyst comprising finely dispersed iridium particles on the silica-containing support under conditions to produce a first reaction product stream comprising at least one paraffin, wherein a method for producing the first catalyst comprises:
      a) treating a silica-containing support with an iridium compound and an organic compound selected from the group consisting of amino acids and hydroxyalkylamines to form a treated support comprising an organic iridium complex on the support;
      b) heating the treated support in an oxidizing atmosphere at a temperature of about 400° C. to partially decompose the organic iridium complex on the support and form a partially decomposed organic iridium complex; and
      c) heating the treated support in a reducing atmosphere at a temperature of about 350° C. to about 500° C. to convert the partially decomposed organic iridium complex into the finely dispersed iridium particles on the silica-containing support;
   (iv) contacting at least a portion of the first reaction product with a second catalyst comprising at least one support and at least one metal component under conditions effective to produce a second reaction product comprising benzene;

(v) separating at least a portion of the second reaction product stream into a benzene recycle stream and a paraffin-rich stream comprising 2-methylpentane and 3-methylpentane; and (vi) recycling at least a portion of the benzene recycle stream to the contacting step (i).

2. The process of claim 1, wherein the partially decomposed organic iridium complex retains between 10 and 95% by weight of the dry weight attributed to the organic iridium complex prior to partial decomposition.

3. The process of claim 1, wherein the partially decomposed organic iridium complex exhibits one or more infra-red absorption bands between 2100-2200 $cm^{-1}$ that are not present in the organic complex before partial decomposition.

4. The process of claim 1, wherein the organic compound comprises one or more of: methanolamine, di-methanolamine, tri-methanolamine, ethanolamine, di-ethanolamine, tri-ethanolamine, butanolamine, di-butanolamine, tri-butanolamine, propanolamine, di-propanolamine, dimethylethanolamine, di-isopropylethanolamine, methyldiethanolamine, dimethylamino-2-propanol, and tri-propanolamine.

5. The process of claim 1, wherein the organic compound comprises tri-ethanolamine.

6. The process of claim 1, wherein the organic compound comprises arginine.

* * * * *